Figure 1:
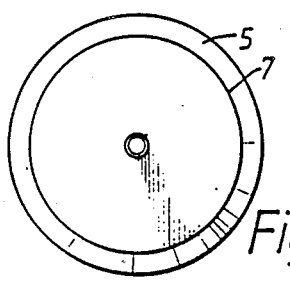

United States Patent [19]

Moreschini

[11] Patent Number: 4,929,180
[45] Date of Patent: May 29, 1990

[54] STAY FULL-EASY LOAD "TURBO" PROPHYLACTIC POLISHING CUP

[76] Inventor: Ronald Moreschini, 2929 7th Ave., Pueblo, Colo. 81008

[21] Appl. No.: 281,321

[22] Filed: Dec. 7, 1988

[51] Int. Cl.⁵ .............................................. A61C 3/06
[52] U.S. Cl. .................................................. 433/166
[58] Field of Search ...................... 433/166; 128/62 A

[56] References Cited

U.S. PATENT DOCUMENTS 4,259,071 5/1981 Warden .............................. 433/166

Primary Examiner—Robert Peshock
Attorney, Agent, or Firm—John W. Huckert; Max Wymore

[57] ABSTRACT

The present invention is a dental prophylactic polishing cup of unique design and shape having uniquely shaped turbine like vanes or ribs positioned at an angle to the long axis of the prophy cup in such a manner, that as the prophy cup is rotated during a dental prophylaxis the polishing paste held in the cup and brought to bear against the surface of the tooth will be acted on by the said turbine like vanes or ribs forcing the polishing paste back into the cup counteracting the forces that tend to dislodge and throw the paste out of the cup. Thus the polishing paste is held in the cup for a longer period of time and for a greater number of revolutions of the cup for greater efficiency reducing the number of times the prophy cup must be refilled or reloaded, saving time effort and materials, and making the whole procedure less messy. The turbine like vanes or ribs also make the prophy cup easier to load or fill as the vanes draw the paste into the cup as it is rotated against the polishing paste container. This prophy cup can be made in many different shapes with many varieties as to number and size of the vanes and manners used to attach said cup to the prophy-angle.

20 Claims, 1 Drawing Sheet

U.S. Patent May 29, 1990 4,929,180

STAY FULL-EASY LOAD "TURBO" PROPHYLACTIC POLISHING CUP

This invention relates generally to devices used in the dental profession and more specifically to devices used in dental prophylaxis.

As part of a dental prophylaxis the teeth are polished by a prophylactic polishing paste that is applied to the teeth by the use of a small rubber cup commonly called a prophy cup. The prophy cup is filled or loaded with the prophylactic polishing paste and then held against the surface of the tooth while being mechanically rotated, this in turn forces the polishing paste to abrade across the surface of the tooth polishing it.

A common problem with known devices of conventional type is the difficulty in retaining the polishing paste within the cup as the cup is rotated against the tooth. The polishing paste is forced out of the cup by centrifical force and the force of being displaced by the tooth. These and other forces tend to fling or throw the paste out of the cup making it necessary to fill the prophy cup many times during a dental prophylactic proceedure. Another common problem with known devices is the difficulty in loading or filling the prophy cup with the polishing paste while engaged with the task of performing a dental prophylaxis.

This invention, an uniquely designed prophy cup having internal ribs or vanes, such as found in some turbines, set at an angle to the long axis of the prophy cup in such a way and design that as the prophy cup is rotated, (in a counter clock wise direction when viewed from the opening of the prophy cup), the vanes will tend to draw anything they come in contact with into the cup, therby counter acting the forces that tend to displace and force the polishing paste out of the cup. Therefore the polishing paste is retained in the prophy cup for a greater number of revolutions decreasing the number of times the prophy cup has to be filled or loaded during a dental prophylactic procedure, This same action of the vanes will tend to draw the prophylactic polishing paste into the cup when it is being loaded or filled with the paste.

The advantage of having the prophylactic polishing paste in the cup for a longer period of time, combined with the greater ease in filling the prophy cup with polishing paste when it does need refilling will result in a savings of both time and effort on the part of the operator doing the prophylactic proceedure.

An object of the present invention is to provide a prophy cup that will save the operator time, effort and materials when performing a dental prophylactic proceedure.

Another object of the present invention is to provide a prophy cup that will waste less and thereby use less prophylactic polishing paste during a dental prophylaxis, saving materials.

Another object of the present invention is to provide a prophy cup that will retain the polishing paste within the cup for a longer period of time and for a greater number of revolutions of the cup thereby reducing the number of times the operator must stop polishing the teeth and refill the cup, thus saving time.

Another object of the present invention is to provide a prophy cup that will be easily filled or loaded with prophylactic polishing paste, thus saving effort.

Another object of the present invention is to provide a prophy cup having internal ribs or vanes designed and set at an angle to the long axis of the prophy cup in such a way that as the prophy cup is rotated the vanes or ribs act upon any thing they come in contact with in such a way that it is drawn into the cup counter acting the forces that tend to force it out of the cup, with a net result of being held in the cup for a longer period of time and a greater number of revolutions of the cup.

Another object of the present invention is to provide a prophy cup having internal vanes set at an angle to the long axis of the cup wherein these vanes are of a small size and many in number and varying to a larger size and fewer in number in an infinate variety for various procedures.

Another object of the present invention is to provide a prophy cup having internal ribs or vanes set at an angle to the long axis of the prophy cup where the vanes would have a cross section of such a design that the leading face of the vane would be perpendicular to the center line of the cup with the back side falling off at a fourty five (45) degree angle giving a buttress like cross section of the vane. The perpendicualr face of the vane would thusly exert a stronger force on the polishing paste while the buttress like trailing portion would best support the leading edge.

Another object of the present invention is to provide a prophy cup that could have a side with a convex shape to better fit the convex shape of most of the portions of the human tooth.

These and other objects and advantages of this invention will become apparent upon reading the following. decription of which the attached drawings form a part.

FIG. 1. Is a screw shank end view of the present invention.

Figure 2:
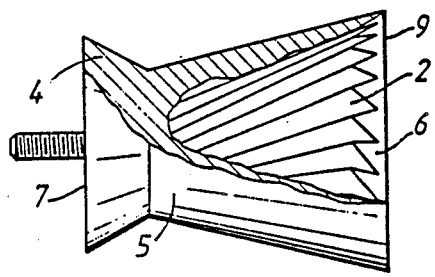

FIG. 2. Is a side view of the present invention with a section removed.

Figure 3:
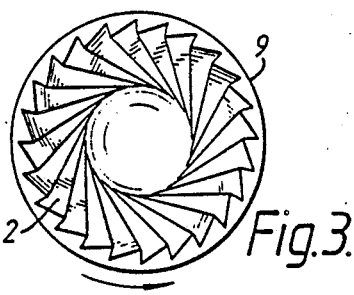

FIG. 3. Is the cup opening end view of the present invention with a curved arrow showing the direction of rotation.

Figure 4:
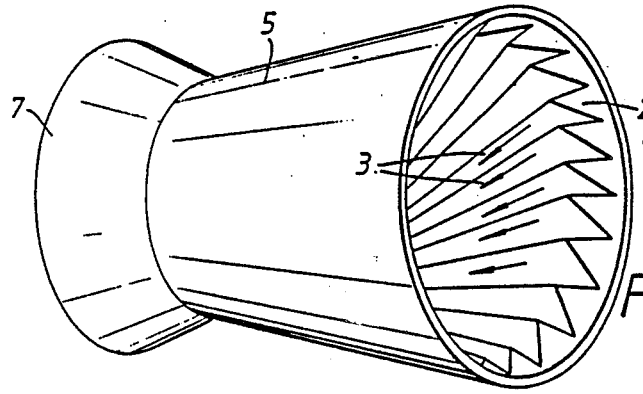

FIG. 4. Is a larger perspective view of the present invention with a curved arrow showing the direction of rotation and five smaller straight arrows showing the resulting force from the rotation.

Figure 5:
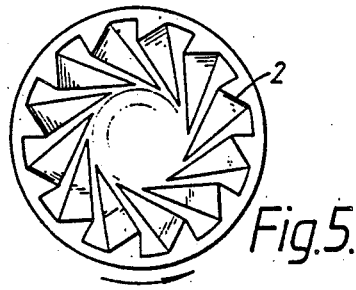
Figure 6:
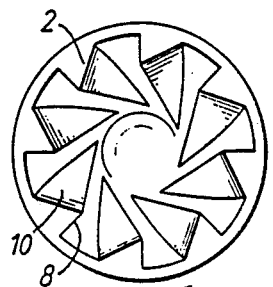
Figure 7:
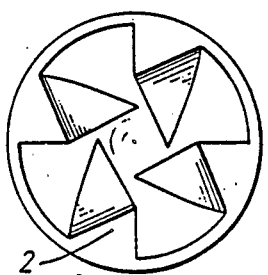

FIG. 5., FIG. 6., and FIG. 7. Are cup end views of the present invention with curved arrows showing the direction of rotation, showing a variety of size and number of the turbine like vanes, and the buttress like shape of the vanes or ribs.

Figure 8:

FIG. 8. Is a side view of the present invention with a convex shape.

Figure 9:

FIG. 9. Is a side view of the present invention with a concave shape.

REFERING TO THE DRAWING

In FIG. 3. it is seen as the prophy cup rotates in the direction of the curved arrow the vanes or ribs 2, form a vortex or turbine like set of vanes which will act upon the prophylactic polishing paste in the cup in such a way as to draw the polishing paste inwrard and downward into the center of the cup as illustrated by the straight arrows 3, in FIG. 4.

Looking at FIG. 2. we see a side view of the present invention with a cross section 4, removed from the prophy cup 5 disclosing the vanes or ribs 2 positioned at an angle to the long axis of the prophy cup 5. FIG. 2. also shows how the angled vanes or ribs 2 are tapered 6, at the cup opening, ending in a thin edge 9 thus allowing the edge of the prophy cup to fit in and under the free margin of the gingiva surrounding the cervical portion of the human tooth to clean and massage the same. Also seen in FIG. 2. is the skirt like projection at the screw shank end of the prophy cup, indicated by number 7. This projection will with the aid of centrifugal force fling off the abrasive polishing paste keeping it out of the gears and bearing of the prophy angle.

FIGS. 5, 6, and 7 show a variety of numbers and sizes of the turbine like vanes or ribs 2 and also show the buttress like shape of the cross section of the vanes 2. In FIG. 6. we can see the perpendicular face 8 of the vanes or ribs 2, and the buttress like shape of the back or trailing edge 10 of the vane or rib 2 which gives the best possible support to the working face 8 of the turbine like vanes or ribs 2.

Looking at FIG. 8. we see a side view of the invention with a convex shaped side to better fit the convex shaped portions of the human tooth. FIG. 9. shows a side view of the present invention with a concave shaped side to better fit the flatter surfaces of the human tooth. For simplicity only the screw shank type prophy cup has been illustrated, but it is understood that the present invention would be applicable for all forms of attaching the prophy cup to the prophy angle such as the screw shank, the latch type and the snap on friction type.

This invention may be further developed within the scope of the following attached claims, accordingly, it is desired that the fore going description be read merely as being illustrative of an operative embodiment of this invention and not in a strictly limiting sense.

What is claimed is:

1. A prophy cup for use with a prophy angle and dental polishing compound comprising: a conically shaped body member, attachment means at the smaller end of said body member, the larger end of said body member having a central opening cavity for holding said polishing compound, and a plurality of internal turbine like vanes or ribs around the inside wall of said cavity, each vane or rib being at a slight angle towards the direction of intended cup rotation so as to hold said compound within the cup cavity during rotation and use thereof.

2. A device as set forth in claim 1 wherein said prophy cup attaches to the prophy-angle with a screw shank.

3. A device as set forth in claim 1 wherin said prophy cup has straight shaped sides.

4. A device as set forth in claim 1 wherin said prophy cup has convex shaped sides.

5. A device as set forth in claim 1 wherin said prophy cup has concave shaped sides.

6. A device as set forth in. claim 1 wherein said prophy cup has many varieties as to number and size of the vanes or ribs on the inside of the cup.

7. A device as set forth in claim 6 wherein said prophy cup is easily loaded or filled due to the shape and position of the vanes or ribs located on the inside surface of the prophy cup.

8. A device as set forth in claim 1 wherein said internal turbine like vanes or ribs each have a front working surface that is perpendicular to the center line of the prophy cup.

9. A device as set forth in claim 8 wherein said internal turbine like vanes or ribs each have a buttress like shaped rear or trailing portion that will best support the perpendicular front working surface of said turbine like vanes or ribs.

10. A device as set forth in claim 9 wherein said internal turbine like vanes or ribs are positioned at an angle to the long axis of the prophy cup in such a manner and way that as the prophy cup is rotated during a dental prophylactic proceedure, the prophylactic polishing paste held in the cup is acted on in such a manner as the force it deeper into the cup holding it there in the cup for a longer period of time and for a greater number of revolutions of the cup, thereby reducing the number of times the operator must stop the dental prophylactic proceedure to reload or refill the prophy cup with the prophylactic polishing paste.

11. A prophy cup for dental use comprising: an elongated, cylindrical body member; attachment means at one end of said body member for affixing same to a prophy angle for suitable rotation and use thereof; an opening at the other end of said body member into a central cavity for holding polishing compound; a plurality of internal vanes on the inside of said cavity; and each vane being slightly angled in the direction of intended cup rotation for retaining said compound within said cavity.

12. The cup of claim 11, wherein each vane is angled so that the vane makes approximately ¼ turn inside the cup.

13. The cup of claim 11, wherein each vane is shaped with one flat face substantially perpendicular to the cup center axis, and another portion slope shaped for adding strengh to said vane.

14. The cup of claim 13, wherein each vane has the outer end thereof tapered to the cup opening so as to end in a thin edge therewith.

15. The cup of claim 13, wherein each vane diverges from the next adjacent vane in the outward direction from the bottom of the cup cavity to the opening thereof.

16. The cup of claim 13, together with a skirt-like projection affixed to the attaching end of said cup for protecting the prophy angle from polishing compound.

17. The cup of claim 13, wherein at least four internal vanes are provided.

18. The cup of claim 13, wherein at least eight internal vanes are provided.

19. The cup of claim 13, wherein at least twelve internal vanes are provided.

20. The cup of claim 13, wherein at least twenty-four internal vanes are provided.

* * * * *